United States Patent [19]

Anderson et al.

[11] 4,094,900
[45] June 13, 1978

[54] METHOD OF PREPARING ARYLOXYBENZOIC AND ARYLTHIOBENZOIC ACIDS

[75] Inventors: Elvin Lowell Anderson, Moorestown, N.J.; Gerald Aloysius Connelly, Darby, Pa.

[73] Assignee: SmithKline Corporation, Philadelphia, Pa.

[21] Appl. No.: 798,283

[22] Filed: May 19, 1977

[51] Int. Cl.² .................. C07C 149/40; C07C 63/33
[52] U.S. Cl. ......................... 260/520 E; 260/516
[58] Field of Search ..................... 260/516, 520 E

[56] References Cited

U.S. PATENT DOCUMENTS

| | | | |
|---|---|---|---|
| 3,105,090 | 9/1963 | Leonard | 260/516 |
| 3,652,665 | 3/1972 | Shen | 260/516 |
| 3,657,431 | 4/1972 | Shen | 260/520 E |
| 3,784,635 | 1/1974 | Theissen | 260/516 |
| 3,941,830 | 3/1976 | Theissen | 260/520 E |

FOREIGN PATENT DOCUMENTS

| | | | |
|---|---|---|---|
| 704,414 | 2/1954 | United Kingdom | 260/516 |

OTHER PUBLICATIONS

Bacon, J.C.S., 1965, 4953–4961.

*Primary Examiner*—James O. Thomas, Jr.
*Assistant Examiner*—Michael Shippen
*Attorney, Agent, or Firm*—Joseph A. Marlino; Richard D. Foggio; William H. Edgerton

[57] ABSTRACT

Novel process for preparing aryloxybenzoic and arylthiobenzoic acids by reacting 2-chlorobenzoic acid with substituted phenols or thiophenols in the presence of an alkali metal iodide and a base.

5 Claims, No Drawings

METHOD OF PREPARING ARYLOXYBENZOIC AND ARYLTHIOBENZOIC ACIDS

This invention relates to a novel process for preparing aryloxybenzoic and arylthiobenzoic acids. These acids are important intermediates for preparing xanthone and thioxanthone compounds which are employed as starting materials in the preparation of xanthene and thioxanthene derivatives having useful pharmacodynamic activity such as, for example, tranquilizing, ataractic or antipsychotic activity. Examples of the above xanthene and thioxanthene compounds are disclosed in U.S. Pat. No. 3,192,204.

More specifically, the invention relates to a process wherein 2-chlorobenzoic acid reacts with a substituted phenol or thiophenol in the presence of an alkali metal iodide and a base to give aryloxybenzoic and arylthiobenzoic acid derivatives represented by the following formula:

Formula 1

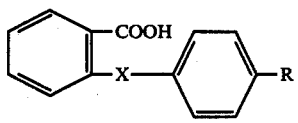

in which:
X is oxygen or sulfur;
R is halo, lower alkyl of from one to four carbons, lower alkoxy of from one to four carbons, trifluoromethyl or thiomethyl.

The above compound of Formula 1 can then be cyclized by treating with concentrated sulfuric acid to form the properly substituted xanthone or thioxanthone.

The prior art process for preparing diaryl ethers is an Ullmann type reaction wherein copper is employed as the catalyst (Bacon et al., J.C.S. 1965, 4953). The starting materials are reacted in the presence of solvents such as collidine or dimethylacetamide. Although the above process is reported to be superior to the conventional Ullmann condensation which is done neat (no solvents), there are many disadvantages associated with it. Employing copper as the catalyst introduces many impurities and by-products. The Ullmann type reaction must have an activated aryl halo substituted compound as the starting material, i.e., the iodide. A further disadvantage of the prior art process is that because of the by-products, isolation of the final product is difficult, usually requiring column chromatography. Relatively low yields and a long reaction time (up to 72 hours) are other disadvantages associated with the prior art process.

It has now been unexpectedly discovered that by employing 2-chlorobenzoic acid as a starting material and substituting an alkali metal iodide, such as sodium iodide for copper as the catalyst, that the above disadvantages of the prior art process can be overcome. The only solvent employed is a substituted phenol or thiophenol. The process of this invention provides a convenient high yield procedure which is completed in a shorter time (7 hours). There are no by-products. Where the prior art process requires active halo compounds such as the iodide, the process of this invention is particularly effective for inactive halogen compounds, i.e., chloro. The 2-chlorobenzoic acid used as the starting material of this novel process is cheaper and more readily available than 2-iodobenzoic acid employed in the prior art process. Finally, because of the clean reaction, isolation of the product is accomplished by the standard method of concentration and recrystallization from an organic solvent.

According to the process of this invention, 2-chlorobenzoic acid is reacted with a substituted phenol or thiophenol using an alkali metal iodide as a catalyst. The reaction is represented as follows:

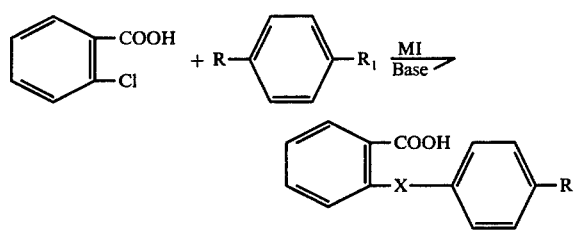

in which:
R is halo, lower alkyl of from one to four carbons, lower alkoxy of from one to four carbons, trifluoromethyl or thiomethyl;
$R_1$ is hydroxy or mercapto;
X is oxygen or sulfur;
M is an alkali metal such as sodium or potassium.

The reaction is carried out using an alkali metal iodide as the catalyst in the presence of a base. Most advantageously sodium iodide is employed as the catalyst. The base is preferably represented by alkali metal hydroxides or alkoxides. Most advantageously sodium hydroxide or sodium methoxide is employed as the basic ingredient. The reaction mixture is heated at from about 150° to 220° C., preferably from about 160° to 180° C. for about 2 to about 20 hours. Most advantageously the reaction mixture is heated for about seven hours.

The following examples illustrate the process of this invention and the preparation of specific compounds but are not to be construed as limitations thereof.

EXAMPLE 1

To a well stirred mixture of 15.7 g. (0.1 mole) of 2-chlorobenzoic acid and 15.0 g. (0.1 mole) of sodium iodide in 250 ml. of 4-chlorophenol was rapidly added a solution of 16 g. (0.4 mole) of sodium hydroxide dissolved in 16 ml. of water. The reaction mixture was heated and concentrated under reduced pressure to an internal temperature of about 145° C. to remove the water and excess 4-chlorophenol. The residue was then stirred at 170° C. for about 7 hours, cooled and diluted with 250 ml. of water. The aqueous solution was extracted with ethyl acetate after acidifying with dilute hydrochloric acid. The ethyl acetate extractions were washed with water, dried and concentrated under reduced pressure. The residue was recrystallized from a benzene-hexane mixture to give pure 2-(4'-chlorophenoxy)benzoic acid, m.p. 114°–115° C.

EXAMPLE 2

Substituting 4-methoxyphenol, 4-thiomethylphenol, 4-methylphenol and 4-trifluoromethylphenol for 4-chlorophenol and following the procedure of Example 1 gives 2-(4'-methoxyphenoxy)benzoic acid, 2-(4'-thiomethylphenoxy)benzoic acid, 2-(4'-methylphenoxy)- benzoic acid and 2-(4'-trifluoromethylphenoxy)benzoic acid respectively.

EXAMPLE 3

To a well stirred mixture of 15.7 g. (0.1 mole) of 2-chlorobenzoic acid and 15.0 g. (0.1 mole) of sodium iodide in 250 ml. of 4-chlorothiophenol was rapidly added a solution of 16 g. (0.4 mole) of sodium hydroxide dissolved in 16 ml. of water. The reaction mixture was heated and concentrated under reduced pressure to an internal temperature of about 145° C. to remove the water and some excess 4-chlorothiophenol. The residue was then stirred at 170° C. for about 7 hours, cooled and diluted with 250 ml. of water. The solution was acidified with dilute hydrochloric acid and extracted with ethyl acetate. The ethyl acetate extractions were washed with water, dried with magnesium sulfate and concentrated under reduced pressure. The residue was recrystallized from a benzene-hexane mixture to give 2-(4'-chlorothiophenoxy)benzoic acid having a melting point of 239°–240° C.

EXAMPLE 4

Similarly substituting 4-methoxythiophenol, 4-thiomethylthiophenol, 4-methylthiophenol, and 4-trifluoromethylthiophenol for 4-chlorothiophenol and following the procedure of Example 3 gives 2-(4'-methoxythiophenoxy)benzoic acid, 2-(4'-thiomethylthiophenoxy)benzoic acid, 2-(4'-methylthiophenoxy)benzoic acid and 2-(4'-trifluoromethylthiophenoxy)benzoic acid respectively.

What is claimed is:

1. A process for preparing aryloxybenzoic and arylthiobenzoic acids of the formula:

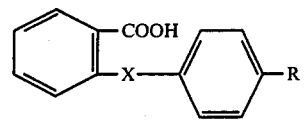

in which:
X is oxygen or sulfur;
R is halo, lower alkyl, lower alkoxy, thiomethyl or trifluoromethyl;
which comprises reacting 2-chlorobenzoic acid with a compound of the formula:

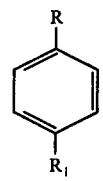

in which:
$R_1$ is hydroxy or mercapto; and
R is halo, lower alkyl, lower alkoxy, thiomethyl or trifluoromethyl;
in the presence of an alkali metal iodide and an alkali metal hydroxide or alkoxide base and heating at a temperature of from about 150° to about 220° C.

2. The process of claim 1 in which the alkali metal iodide is sodium iodide.

3. The process of claim 2 in which $R_1$ is hydroxy and R is halo.

4. The process of claim 3 in which R is chloro.

5. The process of claim 2 in which the base is sodium hydroxide and the temperature is from about 160° to 180° C.

* * * * *